United States Patent [19]

Takase

[11] 3,968,277
[45] July 6, 1976

[54] PROCESS FOR COATING SOLID PARTICLES WITH A DIGESTIVE TRACT-SOLUBLE FILM

[75] Inventor: Muneaki Takase, Tokyo, Japan

[73] Assignee: Zenyaku Kogyo Kabushiki Kaisha, Tokyo, Japan

[22] Filed: Feb. 20, 1974

[21] Appl. No.: 444,056

[30] Foreign Application Priority Data

Feb. 27, 1973 Japan................................. 48-23479
Mar. 13, 1973 Japan................................. 48-29221
Mar. 13, 1973 Japan................................. 48-29222
Mar. 13, 1973 Japan................................. 48-29223

[52] U.S. Cl................................ 427/212; 118/416; 424/32; 424/33; 424/81; 427/242; 427/214; 427/377
[51] Int. Cl.².......................................... C08F 27/08
[58] Field of Search........... 117/100 A; 424/32, 33, 424/81; 427/214, 212, 221, 222, 242, 377; 118/416

[56] References Cited
UNITED STATES PATENTS

| | | | |
|---|---|---|---|
| 2,093,462 | 9/1937 | Malm et al............................ | 260/224 |
| 2,093,464 | 9/1937 | Malm et al............................ | 260/225 X |
| 3,041,243 | 6/1962 | Sugimoto et al...................... | 117/100 X |
| 3,070,509 | 12/1962 | Volker et al......................... | 424/33 |
| 3,282,790 | 11/1966 | Johnson............................... | 424/33 |
| 3,371,015 | 2/1968 | Sjogren et al....................... | 117/100 X |
| 3,477,995 | 11/1969 | Negoro et al........................ | 424/33 X |
| 3,775,537 | 11/1973 | Lehmann et al...................... | 424/81 X |

*Primary Examiner*—Michael R. Lusignan
*Attorney, Agent, or Firm*—Scrivener Parker Scrivener & Clarke

[57] ABSTRACT

A coating process and apparatus for manufacturing of solid particles with digestive tracts-soluble film by rolling water-containing solid particles at high speed, adding a coating liquid and drying them simultaneously.

11 Claims, 4 Drawing Figures

PROCESS FOR COATING SOLID PARTICLES WITH A DIGESTIVE TRACT-SOLUBLE FILM

DETAILED DESCRIPTION OF THE INVENTION:

The present invention relates to both process and apparatus for coating solid particles such as granules, pills and tablets with digestive tracts-soluble film.

The conventional process for coating granules, pills and tablets with a digestive tracts-soluble film, that is, stomach-soluble film, intestine-soluble film, and gastrointestine-soluble film, is applied generally by a apparatus using a coating pan where there is repeated an operation of contacting solid particles with a solution of film coating material (hereinafter called "coating liquid") in a vessel rolling on low speed of drying them. This process, however, has the following demerits:

1. It is impossible to add a large quantity of coating liquid at a time so as to prevent solid particles from sticking with each other. Therefore, a long time is required before finishing.

2. In this process skilled technics are required a uniform film coating at finishing.

3. This process is adverse for the commercial production because of the above-mentioned factors (1) and (2).

4. This process cannot be applied to solid particles of a small diameter.

5. Large expenses are required for warding off denger that may be incured by the leakage of solvent gas resulted from the rolling of a coating pan itself.

6. This process makes product quality low by the loss of original gloss of a film due to a friction on the surface of solid particles, sticking of solid particles with each other, and ununiformity in the quantity of coating on the particles.

Moreover, there has recently been invented a process for spraying a coating liquid on fluidized bed of particles. This process, however, has such demerits as requiring very complicated operating conditions as well as a large quantity of organic solvent to dissolve the coating material. Under these circumstances, the present inventor attempted to develop a coating method with a digestive tracts-soluble film free from such defects as possessed by conventional methods and, after intensive research, discovered the followings:

A solution obtained from dissolving a substance selected from the under-mentioned Group B in a solvent that is a mixture of two substances selected from the undermentioned Group A, is found to possess a property to develop a film as soon as it contacts water, only in the case of a specific combination.

Group A
{ Lower alcohol
  Lower halogenated hydrocarbon
  Lower ketone

Group B
{ Dialkylaminoethyl methacrylate-alkylmethacrylate Copolymer
  Alkylvinyl pyridine-methacrylic acid-alkyl acrylate Copolymer
  Alkyl methacrylate-methacrylic acid copolymer
  Polyvinylacetal dialkylaminoacetate
  Dicarboxylic acid halfester of cellulose acetate As a result of extensive research on a process for utilizing the above-mentioned properties of the coating, the present inventor discovered the followings:

When the said solution of the coating material is poured onto solid particles containing or having an appropriate water on the surface while being rolled on high speed, a film rapidly develop on and surround the surface of the solid particles. A surplus solution is dispersed onto other non-film coated particles. In addition, the coating surrounded the surface of solid particles can be prevented from becoming viscous, if a heated gas necessary for the evaporation of the solvent is sent in simultaneously with the adding of the solution. By continuously repeating the film formation, it is possible to form a film that is soluble in digestive tract and smooth in the surface, within a short period of time. In case the surface of solid particles softens and deforms due to moisture or the solid particles contain components unstable to water, a perfect film can be formed by applying a protective coating using only an appropriate coating liquid as preliminary operation as in conventional methods and then pouring the coating liquid onto the particles while continuously dropping water necessary for film formation.

The present invention was accomplished on the basis of study results above-mentioned for the primary object of providing a process for coating solid particles with digestive tracts-soluble film, which enables within a short period of time the formation of a perfect film by a very much simpler operation than those of conventional methods.

A further object of the present invention is to provide a process for perfect gastric coating, a film soluble only in stomach, within a short time, by a very much simpler operation than those of conventional processes.

Another object of the present invention is to provide a process for perfect enteric coating, a film soluble only in intestines, within a short time by a very much simpler operation than those of conventional processes.

A still further object of the present invention is to provide a process for perfect gastric and enteric coating, a film soluble in both stomach and intestines, within a short time by very much simpler operation than those of conventional processes.

A particular object of the present invention is to provide a apparatus for applying the said coating process, and to provide a coating apparatus where a perfect film coating is possible without being affected by the size distribution of solid particles.

One of the special feature of the coating process of solid particles with digestive tracts-soluble film is to add the coating solution onto the above-mentioned solid particles and dry them simultaneously, while rolling solid particles having an appropriate quantity of water on the surface, at high speed to such an extent that the particles will not be destroyed.

Other special feature of the coating process are as follows:

In case of coating solid particles with stomach-soluble film by the above-mentioned process, as the said coating there is used a solution obtained by dissolving dialkylaminoethyl methacrylate-alkyl methacrylate copolymer or polyvinylacetal dialkylaminoacetate in a mixed solvent of lower ketone and lower halogented hydrocarbon or a mixed solvent of lower ketone and lower alcohol.

In case of coating solid particles with intestine-soluble film, there is used a solution obtained, as the said coating, by dissolving alkyl methacrylate-methacrylic acid copolymer or dicarboxylic acid halfester of cellulose acetate in a mixed solvent of lower ketone and lower alcohol.

In case of coating solid particles with gastrointestine-soluble film, there is used a solution obtained by dissolving alkyl-vinyl pyridine-methacrylic acid-alkyl acrylate copolymer in a mixed solvent of lower halogenated hydrocarbon and lower alcohol.

Further, special feature of the film coating apparatus of the present invention to be used for applying the said film coating process is as follows:

This apparatus is constructed by a rotary disk inscribed with the base of a fixed outer cylinder, a motor for rotating the said rotary disk with a high speed device, a inner cylinder fixed and supported in such a manner that the lower end of the inner cylinder is slightly separated from the upper surface of the said rotary disk at the concentric position inside the outer cylinder, a cover mounted on the said outer cylinder, and feeding pipe of coating liquid, feeding pipe of water, a ventilating pipe and an exhaust pipe attached to the cover.

The followings are given for further concrete explanations about the present invention:

In the film coating process of the present invention, the rolling of solid particles is given by, for instance, the high speed rotation of the rotary disk installed in such situation that it is inscribed to the base of the outer cylinder fixed as mentioned above. The rolling condition is under the control of the nature of the surface of solid particles, the rotating speed of the rotary disk, and the friction inside the outer cylinder. Accordingly, in case that a water content is very low, diameter or form of solid particles is uneven, or solid particles slip on the above-mentioned surfaces of outer cylinder and disk because of the smoothness of particle surface, an appropriate motion can be given by increasing the rotating speed of the disk and attaching to the outer cylinder surface a block board.

The diameter of each solid particle can freely be set at within the range from 1 mm to a size applicable for oral administration. There is no restriction on the surface conditions of particles except that such particles as having concave on the surface may not be coated uniformely. Pills, global granules, tablets and others generally can be used as solid particles.

Solid particles to be film-coated are variable to a considerable extent depending on composition of solvent, its applied quantity and ventilating temperature. It is favourable, however, that the coating should be started in such condition that solid particles have an appropriate water content. When solid particles themselves contain water, they can be film-coated without drying them. This point is different from conventional processes. If solid particles contain no water, water should be added to them according to circumstances. Solid particles tend to stick together and change their moving conditions, when the translocation of water from the inside to the surface of particles delays. In such a case, an appropriate quantity of water may be supplied. As above-mentioned, in case solid particles cannot contain water before film coating, an appropriate quantity of water should be added to them after carrying on a protective coating.

As for water content of solid particles before coating, 15 to 30% by weight water to solid particles will be desirable for stomach-soluble film and intestine-soluble film while 15 to 25% by weight water to solid particles for gastrointestine-soluble film. As for a quantity of water to be added simultaneously with coating, it is 5 to 25% percentage of water by volume to volume of the used solvent for stomach-soluble film, 3 to 20% percentage of water volume to solvent volume for intestine-soluble film and 3 to 10% percentage of water volume to solvent volume for gastrointestine-soluble film.

These coating liquid may be used after a coating material such as titanium oxide, pigment or plasticizer is suspended or dissolved in them.

The lower ketone to be used as one of the mixed solvents means acetone, ethylmethylketone, etc. The lower halogenated hydrocarbon means carbon tetrachloride, chloroform, methylene dichloride, methylchloroform, etc. The lower alcohol means methanol, ethanol, iso-propanol, etc.

Ketone, halogenated hydrocarbon and alcohol other than the above-mentioned are not suitable for solvent, because they raise drying temperature owing to their high boiling points, thus badly affect both solid particles and film, and may make solvent remain in solid particles.

A mixing ratio of the said lower ketone and lower halogenated hydrocarbon or that of lower ketone and lower alcohol can be set at freely within the range of 9:1 to 3:7. However, as a ratio of lower ketone becomes higher, a required quantity of water tends to increase. At a mixing ratio other than the above-mentioned, coating material tends to be hard to dissolve as a ratio of lower halogenated hydrocarbon or lower alcohol becomes higher. And, the strength of a formed film appears to decline as a ratio of lower ketone becomes higher.

Similarly, a mixing ratio of lower alcohol and lower halogenated hydrocarbon can freely be set at within the range of 1:9 to 9:1. However, as a ratio of lower halogenated hydrocarbon becomes higher, a required quantity of water tends to increase. At a mixing ratio other than the above-mentioned, coating material tends to be hard to dissolve as a ratio of lower halogenated hydrocarbon becomes higher, and the formation of film tends to delay, as a ratio of lower alcohol becomes higher.

In other to dry simultaneous with the feed of a coating liquid, a heated gas needed for evaporation of a solvent in the coating liquid should be blown in. Air is the most common for this purpose. In case, however, solid particles may decompose or degenerate by air, an inert gas is recommended. The volume and temperature of a gas to blow in can be selected according to the quantity of solid particles to coat, the type, fed quantity, and feeding speed of coating liquid.

In short, the conditions under which solid particles can keep rolling ideally should be selected. A temperature of a gas about 45° – 65° C is sufficient. Under the ideal coating conditions, not only the temperature of an exhaust gas becomes 10° – 20° C lower than that of a gas to blow in, but also the temperature of the solid particles is kept at about 20° C lower than that of the exhaust gas. The particles coated by the film coating process of the present invention will, if necessary, further be dried by an appropriate method and manufactured into a product. Since the water initially contained in solid particles undergoes azeotropy with an organic solvent during coating process and rapidly evaporates, the temperature of solid particles is kept low. Moreover, drying after film-coating is carried out without difficulty, since inside solid particles there are remained pores that have been made as a result of the rapid translocation of water to the surface, which also is one of the merits of the present invention.

The effects of the present invention are as follows:

1. By an adjustment of the rolling speed of solid particles, the feeding rate of coating liquid, the temperature and flow rate of the blowing air, a film with any desired thickness can be coated easily.

2. Since a film rapidly develops and coats solid particles, a film with an uniform thickness and yet no pinhole is obtainable without difficulty. As a result, the finished surface of particles is smooth and glossy.

3. Simultaneous operation of coating and drying shortens a time required for film coating.

4. For solid particles with a rather large diameter, a coating solution in a high concentration up to the limit can be used. This economizes an organic solvent required and significantly cuts both a required time and cost.

Next, the examples of the process of the present invention are explained referring to figures.

Figure 3:
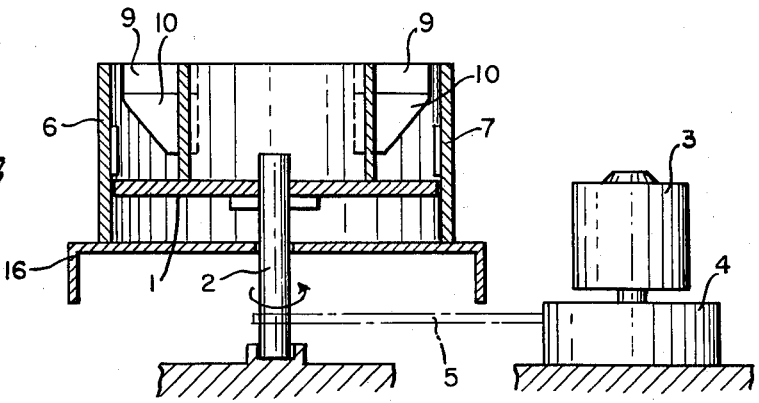
FIG. 3 is a sectional front view of a part of the main body of the film coating apparatus.
Figure 4:
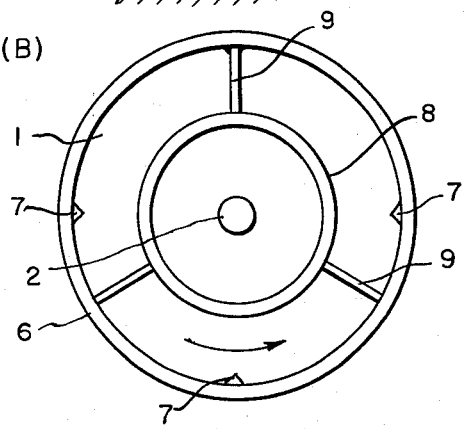

The FIG. 4 is an upper view of the FIG. 3 to X direction showing the interior.

The film coating apparatus used for the film coating process of the present invention has such structure as is indicated by FIGS. 1 to 4. That is to say, 1 in the figure shows a rotary disk. In the examples, a rotary disk made of stainless steel with a diameter of about 23 cm is used. The said disk 1 is inscribed with the lower part of an outer cylinder 6 which is fixed on a mount 16. The said disk 1 is further fixed on a shaft which is rotated by a motor through a single stage transmission 4 and V belt 5.

Figure 1:
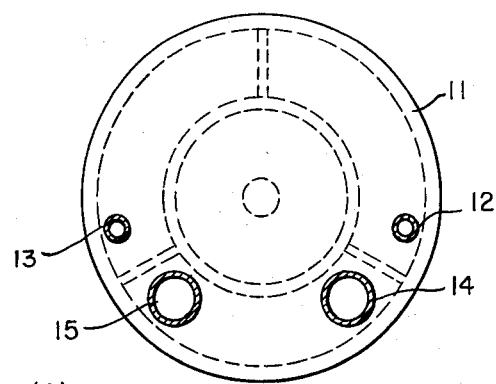
FIG. 1 is a ground plan of the cover section of the film coating apparatus.
Figure 2:
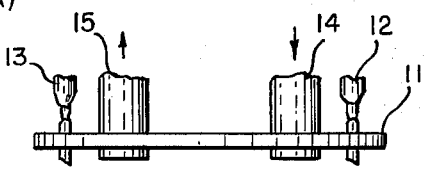
FIG. 2 is a front view of the same.

In the interior surface of the said outer cylinder 6, several block boards 7 (four in the present examples) are mountable but these block boards are demountable according to circumstances. 8 in the figures shows an inner cylinder, which is supported on the said cylinder 6 by means of a supporting plate 9. The said inner cylinder 8 is in the upper position slightly separated from the upper surface of the said disk 1 and concentric to the said outer cylinder 6. The said supporting plates 9 are prepared in plural number -- three in the present examples. In the lower part of each supporting plate 9 there is installed a flexible partition 10 which is movable vertically according to the quantity of fed solid particles. 11 in the figures shows a cover, which is fixed close to both upper ends of the said outer cylinder 6 and the said inner cylinder 8. In the positions of the said cover 11 as are shown in FIGS. 1 and 2, there are installed a feeding pipe of coating solution 12, a feeding pipe of water 13, a ventilating pipe 14, and an exhaust pipe 15.

In place of the said single stage transmission 4, a multistage transmission with many shifting stage can be used. The said inner cylinder 8 may be suspended from the cover 11.

In the said apparatus of film coating, line speed by the rotation of the rotary disk 1 (i.e., peripheral speed) properly is selected by means of single stage transmission 4 according to diameter, shape, surface conditions, and fed quantity of particles, but 200 to 450 m/min. is suitable.

Solid particles to be fed into the apparatus is given a movement toward the rolling direction by the rotation of the rotary disk 1. At the basic part of the flow of solid particles, accelerated and given a centrifugal force, solid particles move toward circumference, since they directly touch the rotary disk 1.

In the circumferential part of the flow of solid particles, solid particles translocate upwards owing to a friction between the interior surface of the outer cylinder 6 and the particles. And the translocated particles roll down to the base on a slope of particles, that is, created from the upper surface of the rotary disk 1 to the interior of the outer cylinder 6 by gravity and centrifugal force.

Therefore, the flow of solid particles rolls toward the advancing direction from the surface to the inside. In this case, an appropriate number of rolls will be 2 to 4 times per rotation. The said number of rolls can be adjusted by the rotating speed of the rotary disk 1 and the mounting or demounting of block boards 7. In the case of particles with smooth surface or small diameter, a desirable rolling motion is obtainable by mounting 2 to 4 block boards.

The inner cylinder 8 assists the formation of a doughnut-shaped high-speed air current caused by the flow of solid particles, prevents the solid particles and coating liquid dispersing into the inside, and plays the role of forming a rolling flow of solid particles.

The flexible partition 10 prevents the heated gas for drying fed through a ventilating pipe 14 blowing out onto the coating section.

The nozzles of the feeding pipe of film-coating liquid 12 and the feeding pipe of water 13 are located around the center of the flow of solid particles. In addition, if the tip of the nozzle is located comparatively near particles, the coating liquid and water can be dispersed smoothly. The ventilating pipe 14 is connected to a blower and a heater.

For carrying out film coating, solid particles are fed into between the outer cylinder 6 and the inner cylinder 8. The rotating disk 1 is rolled by the motor 3 up to a rotating speed enough to form a stable rolling flow of solid particles. A gas at an appropriate temperature is let in through the ventilating pipe 14. Coating liquid and water are continuously fed through a feeding pipes of coating liquid 12 and water 13. In such case that solid particles contain an component that rapidly degenerates by water or solid particles might transform due to the softening of the surface of particles with water, a protective film should be formed by using only a diluted (about 2.5 to 5.0%) coating solution in the present apparatus, and then the said coating should be carried out.

The above-mentioned film coating apparatus has the following merits:

In the said apparatus, moving section consists of only a rotary disk. It provides a coating operation under the sealed condition and thus requires no preventive measure for the leakage of an organic solvent gas.

Another merit is that with the present apparatus a coating can be carried out within a much shorter time than that of conventional coating process because the system can use a remarkably highly concentrated coating solution for tablets, pills, granules with a diameter of more than 2 mm. At the same time, the present apparatus provides a significant cut down in cost by reducing the quantity of solvent to use.

The following examples 1 to 15 are for the coating of stomach-soluble film:

EXAMPLE 1

Glossy, globular granules were obtained by feeding 300 g of globular granules with an average diameter of 1 mm and water content of 24.0% in the said film coating apparatus and continuously adding 180 ml of a 5% solution of polyvinylacetal-diethylaminoacetate in acetone-methylchloroform mixture (7:3) while rotating the rotary disk 1 at the speed of 335 rpm and rapidly letting in an air of 55° C. The exhaust gas temperature was 41° C. The time required for the operation was 20 min. The water content of the granules at the end of coating was 14.6%.

EXAMPLE 2

Glossy, globular granules were obtained by feeding 300 g of globular granules with an average diameter of 1 mm and water content of 24.0% in the said film coating apparatus and continuously adding 180 ml of a 5% solution of polyvinylacetal diethylaminoacetate in acetone-chloroform mixture (7:3) while rotating the rotary disk 1 at the speed of 335 rpm and rapidly letting in an air of 55° C. The exhaust gas temperature was 39° C. The time required for the operation was 16 min. The water content of the granules at the end of coating was 14.0%.

EXAMPLE 3

Glossy pills were obtained by feeding 300 g of pills with an average diameter of 3 mm and water content of 24.0% in the said film coating apparatus and continuously adding 240 ml of a 5% solution of polyvinylacetal diethylaminoacetate in acetone-chloroform mixture (7:3) while rotating the rotary disk 1 at the speed of 335 rpm and rapidly letting in an air of 55° C, and dropping 13.4 ml of water from the point when the pills began to show the sticky tendency. The exhaust gas temperature was 34° C. The time required for the operation was 26 min. The water content of the pills at the end of coating was 25.4%.

EXAMPLE 4

Glossy pills were obtained by feeding 300 g of pills with an average diameter of 3 mm and water content of 24.0% in the said film coating apparatus and continuously adding 240 ml of a 5% solution of polyvinylacetal diethylaminoacetate in acetone-chloroform mixture (3:7) while rotating the rotary disk 1 at the speed of 335 rpm and rapidly letting in an air of 55° C, and dropping 12.6 ml of water from the point when the pills began to show a sticky tendency. The exhaust gas temperature was 35° C. The time required for the operation was 25 min. The water content of the pills at the end of coating was 25.2%.

EXAMPLE 5

Glossy pills were obtained by feeding 300 g of pills with an average diameter of 3 mm and water content of 24.0% in the said film coating apparatus and continuously adding 180 ml of a 5% solution of polyvinylacetal diethylaminoacetate in acetone-methylchloroform mixture (1:1) while rotating the rotary disk 1 at the speed of 335 rpm and rapidly letting in an air of 44° C, and dropping 10.5 ml of water from the point when the pills began to show the sticky tendency. The exhaust gas temperature was 27° C. The time required for the operation was 21 min. The water content of the pills at the end of coating was 23.6%.

EXAMPLE 6

Glossy pills were obtained by feeding 300 g of pills with an average diameter of 5 mm and water content of 24.6% in the said film coating apparatus and continuously adding 120 ml of a 10% solution of polyvinylacetal diethylaminoacetate in acetone-chloroform mixture (7:3) while rotating the rotary disk 1 at the speed of 335 rpm and rapidly letting in an air of 55° C, and, at the same time, dropping 25 ml of water. The exhaust gas temperature was 33° C. The time required for the operation was 12 min. The water content of the pills at the end of coating was 23.5%.

EXAMPLE 7

Glossy tablets were obtained by feeding 300 g of tablets with protective coating and an average diameter of 7 mm in the said film coating apparatus and firstly dropping 5 ml of water and then continuously adding 45 ml of a 10% solution of polyvinylacetal diethylaminoacetate in acetone-ethanol mixture (7:3) while rotating the rotary disk 1 at the speed of 335 rpm and rapidly letting in an air of 34° C. The exhaust gas temperature was 27° C, and the time required for the operation was 15 min.

EXAMPLE 8

Glossy, globular granules were obtained by feeding 300 g of globular granules with an average diameter of 1 mm and water content of 24.0% in the said film coating apparatus and continuously adding 180 ml of a 5% solution of dimethylaminoethyl methacrylate-methyl methacrylate copolymer in acetone-chloroform mixture (7:3) while rotating the rotary disk 1 at the speed of 335 rpm and rapidly letting in an air of 55° C. The exhaust gas temperature was 41° C. The time required for the operation was 17 min. The water content of the granules at the end of coating was 8.4%.

EXAMPLE 9

Glossy, globular granules were obtained by feeding 300 g of globular granules with an average diameter of 1 mm and water content of 24.0% in the said film coating apparatus and continuously adding 180 ml of a 5% solution of dimethylaminoethyl methacrylate-methyl methacrylate copolymer in acetone-methylchloroform mixture (7:3) while rotating the rotary disk 1 at the speed of 335 rpm and rapidly letting in an air of 55° C. The exhaust gas temperature was 40° C. The time required for the operation was 17 min. The water content of the granules at the end of coating was 9.0%.

EXAMPLE 10

Glossy pills were obtained by feeding 300 g of pills with an average diameter of 3 mm and water content of 24.0% in the said film coating apparatus and continuously adding 240 ml of a 5% solution of dimethylaminoethyl methacrylate-methyl methacrylate copolymer in acetone-chloroform mixture (7:3) while rotating disk 1 at the speed of 335 rpm and rapidly letting in an air of 55° C. The exhaust gas temperature was 34° C. The time required for the operation was 20 min. The water content of the pills at the end of coating was 22.0%.

EXAMPLE 11

Glossy pills were obtained by feeding 300 g of pills with an average diameter of 3 mm and water content of 24.0% in the said film coating apparatus and continuously adding 240 ml of a 5% solution of diemthylaminoethyl methacrylate-methyl methacrylate copolymer in acetone-chloroform mixture (3:7) while rotating the rotary disk 1 at the speed of 335 rpm and rapidly letting in an air of 55° C. The time required for the operation was 24 min. The exhaust gas temperature was 34° C. The water content of the pills kept at room temperature for 15 hours after the coating was 5.0%.

EXAMPLE 12

Glossy pills were obtained by feeding 300 g of pills with an average diameter of 5 mm and water content of 24.6% in the said film coating apparatus and continuously adding 240 ml of a 5% solution of dimethyl aminoethyl methacrylate-methyl methacrylate copolymer in acetone-methylchloroform mixture (7:3) while rotating the rotary disk 1 at the speed of 335 rpm and rapidly letting in an air of 55° C. The exhaust gas temperature was 33° C. The time required for the operation was 18 min. The water content of the pills kept at room temperature for 15 hours after coating was 3.0%.

EXAMPLE 13

Glossy pills were obtained by feeding 300 g of pills with an average diameter of 5 mm and water content of 24.6% in the said film coating apparatus and continuously adding 240 ml of a 5% solution of dimethylaminoethyl methacrylate-methyl methacrylate copolymer in acetone-methylchloroform mixture (3:7) while rotating the rotary disk 1 at the speed of 335 rpm and rapidly letting in an air of 55° C. The exhaust gas temperature was 34° C. The time required for the operation was 14 min. The water content of the pills kept at room temperature for 15 hours after coating was 3.4%.

EXAMPLE 14

Glossy pills were obtained by feeding 300 g of pills with an average diameter of 5 mm and water content of 24.6% in the said film coating apparatus and continuously adding 48 ml of a 25% solution of dimethylaminoethyl methacrylate-methyl methacrylate copolymer in acetone-chloroform mixture (7:3) while rotating the rotary disk 1 at the speed of 335 rpm and rapidly letting in an air of 67° C. The exhaust gas temperature was 36° C. The time required for the operation was 4 min. The water content of the pills at the end of coating was 21.0%.

EXAMPLE 15

Glossy tablets were obtained by feeding 300 g of tablets with a diameter of 7 mm and protective coating in the said film coating apparatus and firstly dropping 5 ml of water and then continuously adding 45 ml of a 10% solution of dimethylaminoethyl methacrylate-methyl methacrylate copolymer in acetone-ethanol mixture (7:3) while rotating the rotary disk 1 at the speed of 335 rpm and rapidly letting in an air of 34° C. The exhaust gas temperature was 28° C. The time required for the operation was 16 min.

The examples so far mentioned are for the coating of stomach-soluble film. The following examples 16 to 30 are for the coating of intestine-soluble film.

EXAMPLE 16

Glossy, globular granules were obtained by feeding 150 g of globular granules with an average diameter of 1 mm and water content of 26.0% in the said film coating apparatus and continuously adding 100 ml of a 5% solution of cellulose acetate phtalate in ethanol-acetone mixture (3:7) while rotating the rotary disk 1 at the speed of 580 rpm and rapidly letting in an air of 55° C. The exhaust gas temperature was 43° C. The time required for the operation was 13 min. The water content of the granules at the end of coating was 8.0%.

EXAMPLE 17

Glossy pills were obtained by feeding 500 g of pills with an average diameter of 3 mm and water content of 21.0% in the said film coating apparatus and continuously adding 400 ml of a 5% solution of cellulose acetate phthalate in ethanol-acetone mixture (3:7) while rotating the rotary disk 1 at the speed of 420 rpm and rapidly letting in an air of 65° C. The exhaust gas temperature was 42° C. The time required for the operation was 21 min. The water content of the pills at the end of coating was 5.0%.

EXAMPLE 18

Glossy pills were obtained by feeding 200 g of pills with an average diameter of 5 mm and water content of 21.0% in the said film coating apparatus and continously adding 150 ml of a 5% solution of cellulose acetate phthalate in ethanol-acetone mixture (3:7) while rotating the rotary disk 1 at the speed of 380 rpm and rapidly letting in an air of 60° C. The exhaust gas temperature was 37° C. The time required for the operation was 12 min. The Water content of the pills at the end of coating was 5.0%.

EXAMPLE 19

Glossy pills were obtained by feeding 300 g of pills with an average diameter of 5 mm and water content of 21.0% in the said film coating apparatus and continuously adding 300 ml of a 5% solution of cellulose acetate phthalate in ehtanol-acetone mixture (1:1) while rotating the rotary disk 1 at the speed of 335 rpm and rapidly letting in an air of 65° C. The exhaust gas temperature was 42° C. The time required for the operation was 23 min. The water content of the pills at the end of coating was 5.0%.

EXAMPLE 20

Glossy, globular granules were obtained by feeding 400 g of globular granules with an average diameter of 1 mm and water content of 21.0% and continuously adding 300 ml of a 5% solution of cellulose acetate phthalate in ethanol-acetone mixture (3:7) and then 200 ml of a 5% solution of the same in ethanol-acetone mixture (1:1) while rotating the rotary disk 1 at the speed of 380 rpm and rapidly letting in an air of 65° C. The exhaust gas temperature was 41° C. The time required for the operation was 22 min. The water content of the granules at the end of coating was 5.0%.

EXAMPLE 21

Glossy pills were obtained by feeding 260 g of pills with an average diameter of 5 mm and water content of 24.0% in the said film coating apparatus and continuously adding 65 ml of a 20% solution of cellulose acetate phthalate in ethanol-acetone mixture (1:2) while rotating the rotary disk 1 at the speed of 380 rpm and rapidly letting in an air of 55° C. The exhaust gas temperature was 38° C. The time required for the operation was 4 min. and 30 sec. The water content of the pills at the end of coating was 9.0%.

EXAMPLE 22

Glossy, white pills were obtained by feeding 400 g of pills with an average diameter of 3 mm and water content of 22.0% in the said film coating apparatus and continuously adding a coating liquid obtained by dissolving and suspending 20 g each of cellulose acetate phthalate and titanium oxide in 400 ml of ethanol-acetone mixture (1:1) and, at the same time, dropping 20 ml of water while rotating the rotary disk 1 at the speed of 420 rpm and rapidly letting in an air of 55° C. The exhaust gas temperature was 35° C. The time required for the operation was 23 min. The water content of the pills at the end of coating was 12.6%.

EXAMPLE 23

Glossy tablets were obtained by feeding 300 g of tablets with protective coating and an average diameter of 6 mm in the said film coating apparatus and continuously adding 100 ml of a 10% solution of cellulose acetate phthalate in ethanol-acetone mixture (1:1) and, at the same time, dropping 16 ml of water while rotating the rotary disk 1 at the speed of 380 rpm and rapidly letting in an air of 65° C. The exhaust gas temperature was 50° C. The time required for the operation was 13 min.

EXAMPLE 24

Glossy, white tablets were obtained by feeding 300 g of tablets with protective coating and an average diameter of 6 mm in the said film coating apparatus and continuously adding firstly a coating liquid obtained by dissolving and suspending 10 g of cellulose acetate phthalate and 8 g of titanium oxide in 200 ml of ethanol-acetone mixture (1:1) simultaneously with dropping 14 ml of water, and then similarly 50 ml of a 5% solution of cellulose acetate phthalate in ethanol-acetone mixture (1:1) and 3 ml of water, while rotating the rotary disk 1 at the speed of 380 rpm and rapidly letting in an air of 55° C. The exhaust gas temperature was 40° C, and the time required for the operation was 21 min.

EXAMPLE 25

Glossy, globular granules were obtained by feeding 300 g of globular granules with an average diameter of 1 mm and water content of 24.0% in the said film coating apparatus and continuously adding 180 ml of a 5% solution of methyl methacrylate-methacrylic acid copolymer in ethanol-acetone mixture (3:7) while rotating the rotary disk 1 at the speed of 335 rpm and rapidly letting in an air of 55° C. The exhaust gas temperature was 39° C. The time required for the operation was 14 min. The water content of the granules at the end of coating was 13.0%.

EXAMPLE 26

Glossy pills were obtained by feeding 300 g of pills with an average diameter of 4 mm and water content of 27.6% in the said film coating apparatus and continuously adding 240 ml of a 5% solution of methyl methacrylate-methacrylic acid copolymer in ethanol-acetone mixture (3:7) while rotating the rotary disk 1 at the speed of 335 rpm and rapidly letting in an air of 55° C. The exhaust gas temperature was 32° C. The time required for the operation was 13 min. The water content of the pills at the end of coating was 20.0%.

EXAMPLE 27

Glossy pills were obtained by feeding 300 g of pills with an average diameter of 4 mm and water content of 27.6% in the said film coating apparatus and continuously adding 240 ml of a 5% solution of methyl methacrylate-methacrylic acid copolymer in ethanol-acetone mixture (7:3) while rotating the rotary disk 1 at the speed of 335 rpm and rapidly letting in an air of 55° C. The exhaust gas temperature was 33° C. The time required for the operation was 15 min. The water content of the pills at the end of coating was 20.4%.

EXAMPLE 28

Glossy pills were obtained by feeding 300 g of pills with an average diameter of 4 mm and water content of 27.6% in the said film coating apparatus and continuously adding 120 ml of a 10% solution of methyl methacrylate-methacrylic acid copolymer in ethanol-acetone mixture (3:7) while rotating the rotary disk 1 at the speed of 335 rpm and rapidly letting in an air of 55° C. The exhaust gas temperature was 33° C. The time required for the operation was 7 min. and 20 sec. The water content of the pills at the end of coating was 22.0%.

EXAMPLE 29

Glossy tablets were obtained by feeding 300 g of tablets with protective coating and an average diameter of 6 mm in the said film coating apparatus and continuously adding 120 ml of a 10% solution of methyl methacrylate-methacrylic acid copolymer in ethanol-acetone mixture (3:7) and, at the same time, dropping 12 ml of water, while rotating the rotary disk 1 at the speed of 335 rpm and rapidly letting in an air of 55° C. The exhaust gas temperature was 42° C. The time required for the operation was 16 min.

EXAMPLE 30

Glossy tablets were obtained by feeding 300 g of tablets with protective coating and an average diameter of 7 mm in the said film coating apparatus and firstly dropping 5 ml of water and then continuously adding 150 ml of a 3% solution of methyl methacrylate-methacrylic acid copolymer in ethanol-acetone mixture (2:3) while rotating the rotary disk 1 at the speed of 335 rpm and rapidly letting in an air of 55° C. The exhaust gas temperature was 48° C, and the time required for the operation was 34 min.

The Examples so far mentioned are for the coating of intestine-soluble film. The following examples 31 to 42 are for the coating of gastrointestine-soluble film.

EXAMPLE 31

Glossy pills were obtained by feeding 300 g of pills with an average diameter of 5 mm and water content of 25.4% in the said film coating apparatus and continuously adding 150 ml of a 10% solution of 2-vinyl-5-methyl pyridine-methacrylic acid-methyl acrylate copolymer in ethanol-chloroform mixture (7:3) while rotating the rotary disk 1 at the speed of 335 rpm and rapidly letting in an air of 70° C. The exhaust gas temperature was 42° C. The time required for the operation was 14 min. The water content of the pills at the end of coating was 10.0%.

EXAMPLE 32

Glossy pills were obtained by feeding 310 g of pills with an average diameter of 5 mm and water content of 25.4% in the said film coating apparatus and continuously adding 300 ml of a 5% solution of 2-vinyl-5-methyl pyridine-methacrylic acid-methyl acrylate copolymer in ethanol-chloroform mixture (7:3) while rotating the rotary disk 1 at the speed of 335 rpm and rapidly letting in an air of 70° C. The exhaust gas temperature was 45° C. The time required for the operation was 28 min. The water content of the pills at the end of coating was 6.3%.

EXAMPLE 33

Glossy pills were obtained by feeding 300 g of pills with an average diameter of 3 mm and water content of 25.4% in the said film coating apparatus and continuously adding 200 ml of a 5% solution of 2-vinyl-5-methyl pyridine-methacrylic acid-methyl acrylate copolymer in an ethanol-chloroform mixture (8:2) while rotating the rotary disk 1 at the speed of 335 rpm and rapidly letting in an air of 70° C. The exhaust gas temperature was 44° C. The time required for the operation was 19 min. The water content of the pills at the end of coating was 13.0%.

EXAMPLE 34

Glossy pills were obtained by feeding 300 g of pills with an average diameter of 3 mm and water content of 25.4% in the said film coating apparatus and continuously adding 200 ml of a 5% solution of 2-vinyl-5-methyl pyridine-methacrylic acid-methyl acrylate copolymer in ethanol-chloroform mixture (9:1) while rotating the rotary disk 1 at the speed of 335 rpm and rapidly letting in an air of 50° C. The exhaust gas temperature was 34° C. The time required for the operation was 22 min. The water content of the pills at the end of coating was 16.0%.

EXAMPLE 35

Glossy pills were obtained by feeding 250 g of pills with an average diameter of 3 mm and water content of 25.4% in the said film coating apparatus and continuously adding 200 ml of a 5% solution of 2-vinyl-5-methyl pyridine-methacrylic acid-methyl acryalte copolymer in ethanol-chloroform mixture (1:1) while rotating the rotary disk 1 at the speed of 335 rpm and rapidly letting in an air of 60° C. The exhaust gas temperature was 41° C. The time required for the operation was 17 min. The water content of the pills at the end of coating was 10.2%.

EXAMPLE 36

Glossy pills were obtained by feeding 250 g of pills with an average diameter of 3 mm and water content of 25.4% in the said film coating apparatus and continuously adding 200 ml of a 5% solution of 2-vinyl-5-methyl pyridine-methacrylic acid-methyl acrylate copolymer in ethanol-chloroform mixture (3:7) while rotating the rotary disk 1 at the speed of 335 rpm and rapidly letting in an air of 60° C. The exhaust gas temperature was 39° C. The time required for the operation was 16 min. The water content of the pills at the end of coating was 8.0%.

EXAMPLE 37

Glossy pills were obtained by feeding 300 g of pills with an average diameter of 3 mm and water content of 24.0% in the said film coating apparatus and continuously adding 60 ml of a 25% solution of 2-vinyl-5-methyl pyridine-methacrylic acid-methyl acrylate copolymer in ethanol-methlchloroform mixture (1:2) while rotating the rotary disk 1 at the speed of 420 rpm and rapidly letting in an air of 65° C. The exhaust gas temperature was 42° C. The time required for the operation was 3 min. and 25 sec. The water content of the pills at the end of coating was 8.8%.

EXAMPLE 38

Glossy, globular granules were obtained by feeding 300 g of globular granules with an average diameter of 1 mm and water content of 25.2% in the said film coating apparatus and continuously adding 240 ml of a 5% solution of 2-vinyl-5-methyl pyridine-methacrylic acid-methyl acrylate copolymer in ethanol-chloroform mixture (1:1) while rotating the rotary disk 1 at the speed of 420 rpm and rapidly letting in an air of 55° C. The exhaust gas temperature was 37° C. The time required for the operation was 20 min. The water content of the pills at the end of coating was 16.2%.

EXAMPLE 39

Glossy, globular granules were obtained by feeding 300 g of globular granules with an average diameter of 1 mm and water content of 25.2% in the said film coating apparatus and continuously adding 120 ml of a 10% solution of 2-vinyl-5-methyl pyridine-methacrylic acid-methyl acrylate copolymer in ethanol-chloroform mixture (1:1) while rotating the rotary disk 1 at the speed of 420 rpm and rapidly letting in an air of 55° C. The exhaust gas temperature was 39° C. The time required for the operation was 9 min. The water content of the granules at the end of coating was 19.3%.

EXAMPLE 40

Glossy pills were obtained by feeding 265 g of pills with protective coating and the average diameter of 3 mm in the said film coating apparatus and, while rotating the rotary disk 1 at the speed of 335 rpm and rapidly letting in an air of 55°C, firstly dropping 3 ml of water, secondly continuously adding 40 ml of a 10% solution of 2-vinyl-5-methyl pyridine-methacrylic acid-methylacrylate copolymer in ethanol-chloroform mixture (1:1), and then adding 2 ml of water, 30 ml of coating solution, 1 ml of water and 30 ml of coating solution in order. The exhaust gas temperature was 40° C. The time required for the operation was 9 min.

EXAMPLE 41

Glossy tablets were obtained by feeding 300 g of tablets with protective coating and the average diameter of 6 mm in the said film coating apparatus and, while rotating the rotary disk 1 at the speed of 380 rpm and rapidly letting in an air of 55° C, firstly dropping 3 ml of water, secondly continuously adding 30 ml of a 10% solution of 2-vinyl-5-methyl pyridine-methacrylic acid-methylacrylate copolymer in ethanol-chloroform mixture (1:1) and then adding 2 ml of water, 30 ml of coating solution, 1 ml of water, 30 ml of coating solution, 1 ml of water and 25 ml of coating solution in order. The exhaust gas temperature was 45° C. The time required for the operation was 15 min.

EXAMPLE 42

Glossy, white tablets were obtained by feeding 300 g of tablets with protective coating and the average diameter of 6 mm in the said film coating apparatus and, while rotating the rotary disc 1 at the speed of 380 rpm and rapidly letting in an air of 55°C, firstly dropping 3 ml of water, secondly continuously adding 30 ml of coating solution obtained by dissolving and suspending 7.5 g of 2-vinyl-5-methyl pyridine-methacrylic acid-methylacrylate copolymer and 5 g of titanium oxide in 150 ml of ethanol-chloroform mixture (1:1), thirdly alternately adding 2 ml of water and 30 ml of coating solution till the each total of water and coating solution was 11 ml and 150 ml, fourthly adding 2 ml of water and then adding 20 ml of 5 % solution of 2-vinyl-5-methylpyridine-methacrylic acid-acrylic acid copolymer in ethanol-chloroform mixture (1:1). The exhaust gas temperature was 38° to 40°C. The time required for the operation was 19 min.

What we claim is:

1. A process for coating solid particles with a digestive tract-soluble film which comprises causing solid particles having a water content in the range of from 15 to 30% by weight of water to said particles to roll by a rotating disk rotating at a sufficient speed to provide a peripheral speed of from 200 to 450 meters per minute and applying a coating solution containing a digestive tract-soluble material selected from the group consisting of dialkylamino-ethyl methacrylate-alkylmethacrylate copolymers, alkylvinyl pyridine-methacrylic acid-alkyl acrylate copolymers, alkyl methacrylate-methacrylic acid copolymers, polyvinylacetal dialkylaminoacetate, and dicarboxylic acid halfester of cellulose acetate in a mixed solvent of at least two solvents selected from the group consisting of lower alcohols, lower ketones and lower halogenated hydrocarbons to said rolling particles and developing a digestive tract-soluble film on said particles while subjecting said particles to heated gas to evaporate said solvent therefrom.

2. The process for coating solid particles with stomach soluble film according to claim 1, wherein said coating solution comprises dialkylaminoethyl methacrylate-alkyl methacrylate copolymer in mixed solvent of lower ketone and lower halogenated hydrocarbon.

3. The process for coating solid particles with stomach-soluble film according to claim 1, wherein said coating solution comprises dialkylaminoethyl methacrylate-alkyl methacrylate copolymer in mixed solvent of lower ketone and lower alcohol.

4. The process for coating solid particles with stomach-soluble film according to claim 1, wherein said coating solution comprises polyvinylacetal dialkylaminoacetate in mixed solvent of lower ketone and lower halogenated hydrocarbon.

5. The process for coating solid particles with stomach-soluble film according to claim 1, wherein said coating solution comprises polyvinylacetal dialkylaminoacetate in mixed solvent of lower ketone and lower alcohol.

6. The process for coating solid particles with intestine-soluble film according to claim 1, wherein said coating solution comprises alkyl methacrylate-methacrylic acid copolymer in mixed solvent of lower ketone and lower alcohol.

7. The process for coating solid particles with intestine-soluble film according to claim 1, wherein said coating solution comprises dicarboxylic acid halfester of cellulose acetate in mixed solvent of lower ketone and lower alcohol.

8. The process for coating solid particles with gastro-intestine-soluble film according to claim 1, wherein said coating solution comprises alkyl vinyl pyridine-methacrylic acid-alkyl acrylate copolymer in mixed solvent lower halogenated hydrocarbon and lower alcohol.

9. The process of claim 1 wherein the solid particles are sensitive to water and they are pretreated with a protective coating, the necessary water being added simultaneously with the coating solution.

10. The process of claim 1 wherein the digestive tract-soluble film forming solute is present in an amount of from 5 to 25% and the temperature of the heated gas is from about 45° to 60°C, and wherein said coating operation is performed for less than about 35 minutes.

11. The process of claim 1, wherein the mixed solvent is a mixture of a lower ketone and lower halogenated hydrocarbon or lower alcohol with a mixing ratio of lower ketone to lower alcohol or halogenated hydrocarbon of between 9:1 to 3:7 or a mixture of a lower alcohol and lower halogenated hydrocarbon having a mixing ratio of lower alcohol to lower halogenated hydrocarbon of between 1:9 and 9:1.

* * * * *